United States Patent
Pastore et al.

(10) Patent No.: US 7,065,405 B2
(45) Date of Patent: Jun. 20, 2006

(54) STRESS REDUCTION PACING MODE FOR ARRHYTHMIA PREVENTION

(75) Inventors: Joseph M. Pastore, Minneapolis, MN (US); Steven D. Girouard, Woodbury, MN (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 580 days.

(21) Appl. No.: 10/298,156

(22) Filed: Nov. 15, 2002

(65) Prior Publication Data

US 2004/0098057 A1    May 20, 2004

(51) Int. Cl.
*A61N 1/362*    (2006.01)
(52) U.S. Cl. ........................................... 607/9
(58) Field of Classification Search ............. 607/9, 607/13–14, 17–18, 25
See application file for complete search history.

(56) References Cited

U.S. PATENT DOCUMENTS

| | | | |
|---|---|---|---|
| 4,354,497 A | 10/1982 | Kahn | |
| 4,554,922 A | 11/1985 | Prystowsky et al. | |
| 4,872,459 A | 10/1989 | Pless et al. | |
| 4,880,005 A | 11/1989 | Pless et al. | |
| 5,174,289 A | 12/1992 | Cohen | |
| 5,267,560 A | 12/1993 | Cohen | |
| 5,334,222 A | 8/1994 | Salo et al. | |
| 5,417,717 A | 5/1995 | Salo et al. | |
| 5,514,161 A | 5/1996 | Limousin | |
| 5,584,867 A | 12/1996 | Limousin et al. | |
| 5,584,868 A | 12/1996 | Salo et al. | |
| 5,792,203 A | 8/1998 | Schroeppel | |
| 5,797,970 A | 8/1998 | Pouvreau | |
| 5,995,871 A | 11/1999 | Knisley | |
| 6,151,524 A | 11/2000 | Krig et al. | |
| 6,223,082 B1 | 4/2001 | Bakels et al. | |
| 6,272,377 B1 | 8/2001 | Sweeney et al. | |
| 6,278,894 B1 | 8/2001 | Salo et al. | |
| 6,285,898 B1 | 9/2001 | Ben-Haim | |
| 6,363,279 B1 | 3/2002 | Ben-Haim et al. | |
| 6,427,084 B1 | 7/2002 | Baker et al. | |
| 6,628,988 B1* | 9/2003 | Kramer et al. ............ 607/9 |
| 6,915,160 B1 | 7/2005 | Auricchio et al. | |
| 2002/0045809 A1* | 4/2002 | Ben-Haim ............... 600/374 |
| 2002/0161410 A1 | 10/2002 | Kramer et al. | |
| 2003/0023278 A1 | 1/2003 | Pastore et al. | |
| 2003/0187482 A1 | 10/2003 | Pastore et al. | |
| 2003/0208240 A1 | 11/2003 | Pastore et al. | |
| 2003/0233132 A1 | 12/2003 | Pastore et al. | |
| 2004/0044374 A1 | 3/2004 | Weinberg et al. | |
| 2004/0054381 A1 | 3/2004 | Pastore et al. | |
| 2004/0098057 A1 | 5/2004 | Pastore | |
| 2004/0116970 A1 | 6/2004 | Girouard et al. | |
| 2005/0065568 A1 | 3/2005 | Liu et al. | |

FOREIGN PATENT DOCUMENTS

EP    0522693    1/1993

(Continued)

*Primary Examiner*—Carl H. Layno
(74) *Attorney, Agent, or Firm*—Schwegman, Lundberg, Woessner & Kluth, P.A.

(57) ABSTRACT

An apparatus and method preventing cardiac arrhythmias with pacing therapy is disclosed. Upon detection of a pre-arrhythmic condition, an implantable cardiac rhythm management device is configured to deliver pacing therapy in a manner that pre-excites particular myocardial sites that have been identified as stressed sites and likely locations for the origination of arrhythmias. Such pacing results in a reduction in myocardial wall stress at those sites during systole and reduces the probability of an arrhythmia occurring.

19 Claims, 3 Drawing Sheets

FOREIGN PATENT DOCUMENTS

| | | |
|---|---|---|
| EP | 1197243 A2 | 4/2002 |
| WO | WO-97/25098 | 7/1997 |
| WO | WO-00/04947 | 2/2000 |
| WO | WO-00/09206 | 2/2000 |
| WO | WO-01/08748 | 2/2001 |
| WO | WO-01/30436 | 5/2001 |

* cited by examiner

STRESS REDUCTION PACING MODE FOR ARRHYTHMIA PREVENTION

FIELD OF THE INVENTION

This invention pertains to apparatus and methods for the diagnosis and treatment of heart disease and to devices providing electrostimulation to the heart such as cardiac pacemakers.

BACKGROUND

Tachyarrhythmias are abnormal heart rhythms characterized by a rapid heart rate, typically expressed in units of beats per minute (bpm). They can occur in either chamber of the heart (i.e., ventricles or atria) or both. Examples of tachyarrhythmias include sinus tachycardia, ventricular tachycardia, ventricular fibrillation (VF), atrial tachycardia, and atrial fibrillation (AF). Tachyarrhythmias can be due to abnormal excitation by normal pacemaker tissue, an ectopic excitatory focus, or a re-entry phenomenon. Tachycardia occurs when the heart contracts relatively normally but at a rapid rate, while fibrillation occurs when the chamber depolarizes in a chaotic fashion with abnormal depolarization waveforms as reflected by an EKG.

An electrical defibrillation shock applied to a heart chamber can be used to terminate most tachyarrhythmias by depolarizing excitable myocardium and rendering it refractory. Implantable cardioverter/defibrillators (ICDs) provide this kind of therapy by delivering a shock pulse to the heart when fibrillation is detected by the device. ICDs can be designed to treat either atrial or ventricular tachyarrhythmias, or both, and may also incorporate cardiac pacing functionality. The most dangerous tachyarrhythmias are ventricular tachycardia and ventricular fibrillation, and ICDs have most commonly been applied in the treatment of those conditions. Another type of electrical therapy for tachycardia is anti-tachycardia pacing (ATP). In ATP, the heart is competitively paced with one or more pacing pulses in an effort to interrupt the reentrant circuit causing the tachycardia. Modern ICD's usually have ATP capability so that ATP therapy is delivered to the heart when a tachycardia is detected, while a shock pulse is delivered when fibrillation occurs.

ICDs are also capable of detecting atrial tachyarrhythmias, such as atrial fibrillation and atrial flutter, and delivering a shock pulse to the atria in order to terminate the arrhythmia. Although not immediately life-threatening, it is important to treat atrial fibrillation for several reasons. First, atrial fibrillation is associated with a loss of atrio-ventricular synchrony which can be hemodynamically compromising and cause such symptoms as dyspnea, fatigue, vertigo, and angina. Atrial fibrillation can also predispose to strokes resulting from emboli forming in the left atrium. Although drug therapy and/or in-hospital cardioversion are acceptable treatment modalities for atrial fibrillation, ICDs configured to treat atrial fibrillation offer a number of advantages to certain patients, including convenience and greater efficacy.

As described above, an implantable cardiac rhythm management device may deliver appropriate therapy to terminate certain detected arrhythmias. Such therapies are not invariably successful, however, and, even when they are, may require repeated application until the arrhythmia is finally terminated. Defibrillation shocks also subject the patient to some discomfort. It would be more beneficial if an implantable device could detect when a pre-arrhythmic condition exists and deliver electro-stimulatory therapy in a manner that prevents the arrhythmia from occurring in the first instance.

SUMMARY OF THE INVENTION

One factor responsible for the initiation of arrhythmias in the heart is the mechanical stress exerted on vulnerable regions of the heart during systolic contraction. The present invention relates to an apparatus and method for relieving such stresses by applying pacing therapy in a manner that mechanically unloads one or more selected myocardial regions during systole relative to other regions. Disparate stresses in different areas of the heart are also responsible for undesirable myocardial remodeling in heart failure patients. Although pacing therapy to unload stressed myocardial regions may be beneficial in preventing or reversing such remodeling, it may not be desirable to continually employ such pacing therapy in certain patients because that may not be the most hemodynamically effective way for the heart to beat. It may also not be desirable to continuously pace at a pacing rate that is optimal for relieving myocardial wall stress in order to prevent arrhythmias. In accordance with the present invention, a cardiac rhythm management device is configured to switch to a stress reduction mode and deliver pacing therapy which mechanically unloads one or more identified stressed myocardial regions upon detection of a pre-arrhythmic condition. When no such pre-arrhythmic condition exists, the device may employ another mode of pacing, such as conventional bradycardia or resynchronization pacing, or may not deliver any pacing therapy at all.

DETAILED DESCRIPTION

It is known that in certain patients, cardiac arrhythmias tend to arise in particular myocardial regions when those regions are subjected to mechanical and/or hypoxic stresses such as occur during systolic contractions. In accordance with the present invention, multi-site pacing is used to change the distribution of wall stress experienced by the ventricle during systole in order to mechanically unload those vulnerable regions and render them less likely to initiate an arrhythmia. An implanted cardiac rhythm management device may be configured to deliver such pacing therapy in response to the occurrence of a pre-arrhythmic condition as detected by a variety of means.

1. Stress Reduction Pacing Therapy

The degree to which a heart muscle fiber is stretched before it contracts is termed the preload. The maximum tension and velocity of shortening of a muscle fiber increases with increasing preload. The increase in contractile response of the heart with increasing preload is known as the Frank-Starling principle. When a myocardial region contracts late relative to other regions, the earlier contraction of opposing regions stretches the later contracting region and increases its preload. The degree of tension or stress on a heart muscle fiber as it contracts is termed the afterload.

Because pressure within the ventricles rises rapidly from a diastolic to a systolic value as blood is pumped out into the aorta and pulmonary arteries, the part of the ventricle that first contracts does so against a lower afterload than does a part of the ventricle contracting later. Thus, a myocardial region that contracts earlier than other regions during systole is subjected to both a decreased preload and a decreased afterload. What is referred to herein as stress reduction pacing or pre-excitation pacing makes use of this phenomena in order to redistribute myocardial wall stress during systole by pacing one or more sites in a ventricle (or an atrium) with one or more pacing pulses delivered in a specified pulse output sequence. The pace or paces are delivered in a manner that excites a previously stressed region of the myocardium earlier during systole so that it experiences less afterload and preload. This pre-excitation of the previously stressed region relative to other regions unloads the region from mechanical stress, making it less likely that the cells in that region will exhibit inherent intrinsic activity and cause an arrhythmia. An increased preload and afterload also requires an increased energy expenditure by the muscle which, in turn, increases its perfusion requirements and may result in ischemia. Pre-excitation of an ischemic region may thus reduce the region's need for blood as well as reduce the mechanical stress to which the region is subjected during systole to reduce the likelihood of an arrhythmia.

Pre-excitation pacing can also have a beneficial effect in the treatment of heart failure. The conduction delays associated with heart failure and ventricular dysfunction cause different regions of the myocardium to contract later than others and thus subject those regions to increased stress during systole. The heart's initial physiological response to the uneven stress resulting from an increased preload and afterload is compensatory hypertrophy in those later contracting regions of the myocardium. In the later stages of remodeling, the regions may undergo atrophic changes with wall thinning due to the increased stress. This process is referred to as cardiac remodeling and is strongly associated with increased mortality in heart failure patients. In addition to its anti-arrhythmic effects, pre-excitation pacing of previously stressed or hypertrophied myocardial regions may also prevent or reverse such remodeling.

Pre-excitation pacing as described above is preferably delivered in conjunction with a conventional synchronous pacing mode such as used for treating bradycardia. If functioning properly, an implanted pacemaker makes up for the heart's inability to pace itself at an appropriate rhythm in order to meet metabolic demand by enforcing a minimum heart rate. Cardiac rhythm management devices have also been developed for the treatment of heart failure that provide multi-site pacing stimulation to one or more heart chambers in an attempt to improve the coordination of atrial and/or ventricular contractions, termed cardiac resynchronization therapy. In multi-site resynchronization pacing, the atria or ventricles are paced at more than one site in order to affect a spread of excitation that results in a more coordinated contraction. Biventricular pacing is one example of multi-site pacing in which both ventricles are paced in order to synchronize their respective contractions.

A patient suitable for treatment with pre-excitation pacing therapy for arrhythmia prevention may also benefit from bradycardia and/or resynchronization pacing. In those situations, however, the optimum manner for delivering bradycardia or resynchronization therapies in any particular patient may be inconsistent with the optimum manner for delivering pre-excitation pacing in order to prevent arrhythmias. In the case of resynchronization pacing, the particular pacing sites and pacing pulse timing used to improve the hemodynamics of a heart failure patient may be different than the pacing sites and pacing pulse timing for optimal application pre-excitation therapy to prevent arrhythmias. For example, a more hemodynamically effective contraction may be obtained by exciting a number of selected pacing sites simultaneously in some patients, which may not result in the pre-excitation of previously stressed myocardium. Pre-excitation pacing is also only effective during cardiac cycles in which pre-excitation paces are delivered. Pre-excitation pacing is thus optimally delivered in conjunction with a synchronous bradycardia pacing mode where the escape interval or intervals are such that the pacing rate is greater than the intrinsic heart rate. It may not be desirable, however, to employ such overdrive pacing on a continuous basis. It may not even be desirable for some patients to be paced at all on a continuous basis. To deal with these situations, a cardiac rhythm management device as described below may be configured to deliver optimal pre-excitation therapy for arrhythmia prevention only upon detection of a pre-arrhythmic condition.

2. Hardware Platform

Cardiac rhythm management devices such as pacemakers are usually implanted subcutaneously on a patient's chest and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

Figure 1:
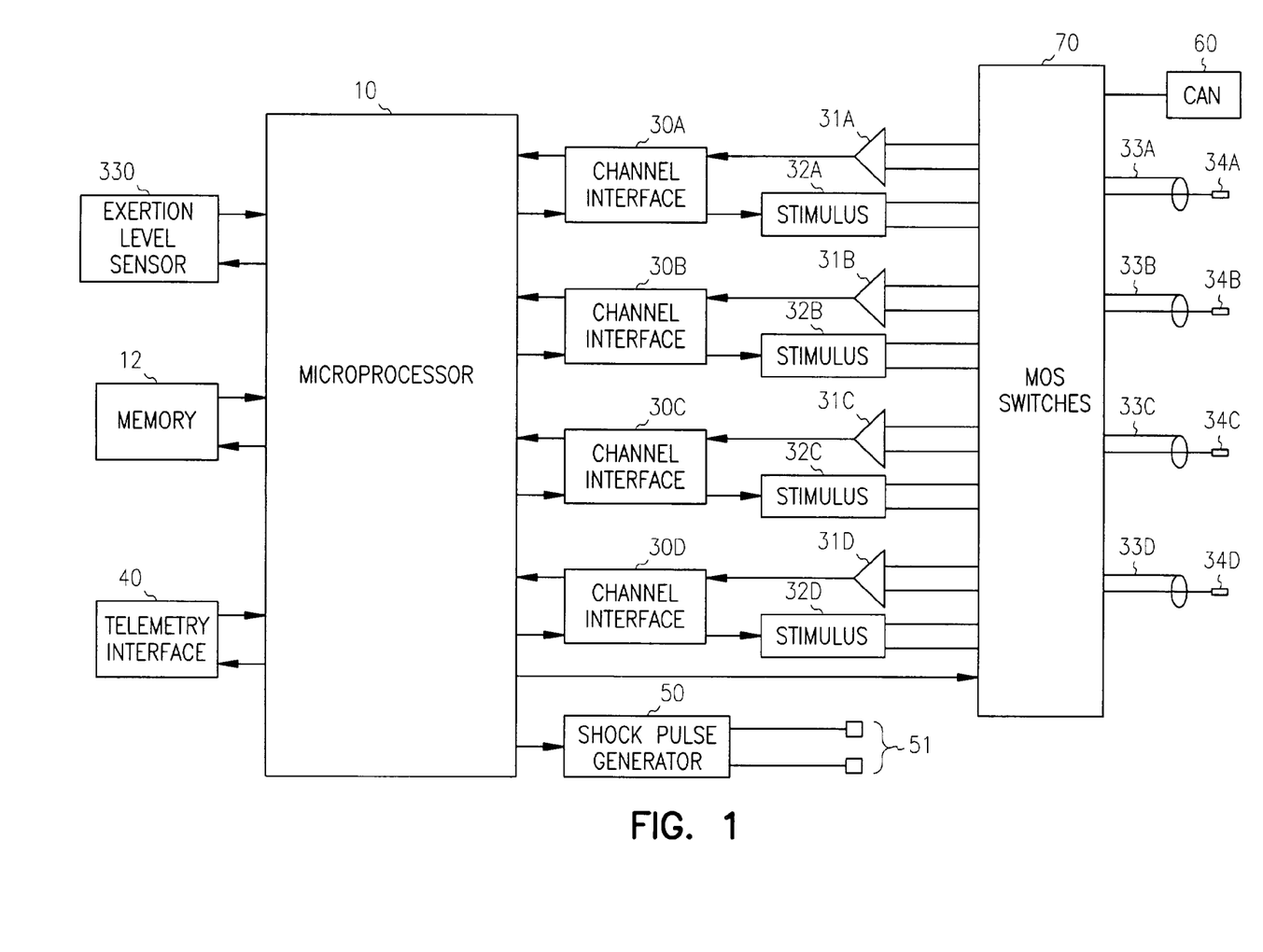
FIG. 1 is a block diagram of an exemplary cardiac rhythm management device for practicing the present invention.

FIG. 1 shows a system diagram of a microprocessor-based cardiac rhythm management device or pacemaker suitable for practicing the present invention. The device is equipped with multiple sensing and pacing channels which may be physically configured to sense and/or pace multiple sites in the atria or the ventricles. The controller 10 of the pacemaker is a microprocessor which communicates with a memory 12 via a bidirectional data bus. The memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor.

Shown in the figure are four exemplary sensing and pacing channels designated "a" through "d" comprising bipolar leads with ring electrodes 33*a*–*d* and tip electrodes 34*a*–*d*, sensing amplifiers 31*a*–*d*, pulse generators 32*a*–*d*, and channel interfaces 30*a*–*d*. Each channel thus includes a pacing channel made up of the pulse generator connected to the electrode and a sensing channel made up of the sense amplifier connected to the electrode. The channel interfaces 30*a*–*d* communicate bidirectionally with microprocessor 10, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively.

The electrodes of each bipolar lead are connected via conductors within the lead to a MOS switching network 70 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing or can 60 serving as a ground electrode. As explained below, one way in which the device may alter the spatial distribution of pacing is to switch from unipolar to bipolar pacing (or vice-versa) or to interchange which electrodes of a bipolar lead are the cathode and anode during bipolar pacing. A shock pulse generator 50 is also interfaced to the controller for delivering a defibrillation shock via a pair of shock electrodes 51 to the atria or ventricles upon detection of a shockable tachyarrhythmia.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. An exertion level sensor 330 (e.g., an accelerometer, a minute ventilation sensor, or other sensor that measures a parameter related to metabolic demand) enables the controller to adapt the pacing rate in accordance with changes in the patient's physical activity. A telemetry interface 40 is also provided which enables the controller to communicate with an external programmer.

The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. Multiple excitatory stimulation pulses can be delivered to multiple sites during a cardiac cycle in order to both pace the heart in accordance with a bradycardia mode and provide pre-excitation of selected sites.

The device shown in FIG. 1 can be configured for stress reduction pacing such that one or more cardiac sites are sensed and/or paced in a manner that pre-excites at least one region of the myocardium that has been identified to be stressed and prone to the generation of arrhythmias. In accordance with the invention, the device is configured to undergo a mode switch upon detection of a pre-arrhythmic condition to a stress reduction mode in which such stress reduction pacing is delivered.

Switching to the stress reduction mode may include altering the device's pacing pulse output configuration and/or pulse output sequence in order to pre-excite a stressed myocardial region, where the pulse output configuration specifies a specific subset of the available electrodes to be used for delivering pacing pulses and the pulse output sequence specifies the timing relations between the pulses. The pulse output configuration is defined by the controller selecting particular pacing channels for use in outputting pacing pulses and by selecting particular electrodes for use by the channel with switch matrix 70. A switch to the stress reduction mode may also include adjusting one or more pacing parameters such as the escape intervals that determine pacing rate in order to pace the heart more frequently. In a normal operating mode, when no pre-arrhythmic condition is present, the device may either deliver no therapy at all or deliver a pacing therapy with a different pacing configuration, a different pulse output sequence, and/or different pacing parameter settings.

3. Identification of Stressed Myocardial Sites

Figure 2:
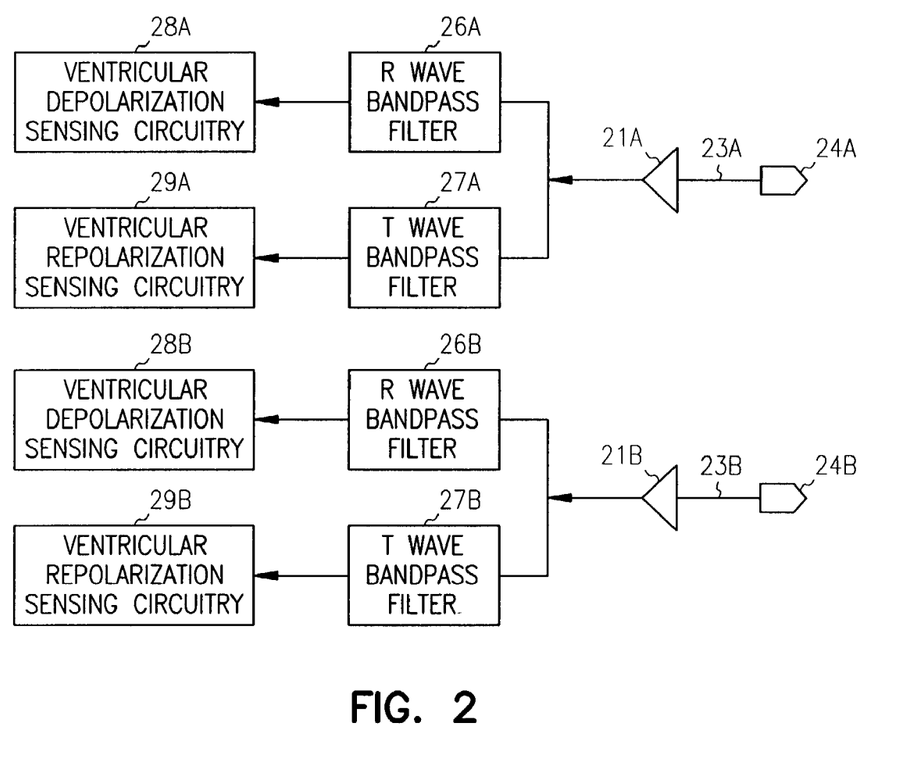
FIG. 2 is a block diagram of sensing channel components for detecting ventricular depolarizations and repolarizations.

Stressed myocardial sites to which pre-excitation pacing is to be applied in the stress reduction mode may be identified clinically by a variety of means, including anatomical information gained from imaging studies and electrophysiologic testing. The device shown in FIG. 1 can also be configured to determine the extent of stress at those sites where its sensing/pacing electrodes are disposed after implantation. It is known that the action potential duration of a myocardial fiber decreases with mechanical stress. The collective action potential duration of a myocardial region during systole, also referred to herein as the activation-recovery interval, can be measured as the time between a detected depolarization and a detected repolarization in an electrogram generated by a sensing channel. Sensing channels can be designed to detect both depolarizations (i.e., conventional atrial or ventricular senses) and repolarizations. FIG. 2 illustrates how this may be implemented in a ventricular sensing channel. When the channel is awaiting a ventricular sense, the electrogram signal is passed through an R wave bandpass filter (26a or 26b) with passband characteristics selected to match the frequency content of a ventricular depolarization. The ventricular depolarization sensing circuitry (28a or 28b) then compares the filtered electrogram signal with a threshold to detect when a ventricular sense occurs. After a ventricular sense occurs, the channel awaits a ventricular repolarization during a specified time frame (e.g., between 50 and 500 milliseconds after the ventricular depolarization). During this time, the electrogram signal is passed through a T wave bandpass filter (27a or 27b) that has a passband characteristic conforming to the frequency content of a ventricular repolarization which is generally lower than that of a ventricular depolarization. The ventricular repolarization sensing circuitry (29a or 29b) then compares the filtered electrogram signal with a threshold to determine when the repolarization occurs. The channel may continue to monitor for depolarizations during this time in case the repolarization is undersensed. A similar scheme with atrial depolarization and repolarization bandpass filters and sensing circuits may be implemented to detect atrial repolarizations.

The bandpass filters in FIG. 2 may be implemented as analog filters that operate directly on the electrogram signal received from the electrodes or may be switched capacitor-type filters that sample the electrogram signal into a discrete-time signal which is then filtered. Alternatively, the electrogram signal can be sampled and digitized by an A/D converter in the channel interface with the bandpass filtering implemented in the digital domain by a dedicated processor or code executed by the controller 10.

After measuring the activation-recovery interval at a plurality of myocardial sites, sites that are stressed may be identified with a specified threshold criterion applied to the activation-recovery interval. That is, a site is identified as stressed when its measured activation-recovery interval is below the specified threshold value. Because the cardiac action potential normally varies with heart rate, it may be desirable to measure activation-recovery intervals during intrinsic beats for the purpose of assessing myocardial stress only when the heart rate is within a specified range. Activation-recovery intervals can also be measured during paced beats while pacing pulses are delivered at a specified rate. In the case of a paced beat, the depolarization corresponds to an evoked response detected by the sensing channel, while the repolarization is similar to an intrinsic beat. Alternatively, the threshold criterion for assessing myocardial wall stress based upon the activation-recovery interval may be adjusted in accordance with the measured intrinsic heart rate or pacing rate.

4. Detection of Pre-Arrhythmic Conditions

A pre-arrhythmic condition for triggering the stress reduction mode is any condition deemed to increase the probability of an atrial or ventricualr arrhythmia occurring. As described below, the controller of the device may be programmed to detect such conditions form information gathered by the sensing channels used to detect cardiac activity as well as other available sensing modalities.

a. Ectopic Beat Frequency

An increase in the frequency of ectopic heart beats is known to precede the development of arrhythmias in certain circumstances. The device may therefore be configured to switch to the stress reduction mode when the frequency of detected ectopic beats, such as pre-mature ventricular contractions or PVC's, rises above a specified threshold level.

b. Assessment of Sympathetic Activity

It is well-known that an increase in the activity of the sympathetic nervous system can make the onset of such arrhythmias more likely and may serve as a trigger for such events in certain patients. The level of sympathetic activity may be assessed by monitoring the heart rate via a ventricular sensing channel so that increased sympathetic activity is detected when the time interval between successive ventricular senses (i.e., RR intervals) falls below a specified minimum threshold value. The level of sympathetic activity may be more specifically assessed, however, by measuring the variability of the heart rate which is known to be influenced by the relative levels of sympathetic and parasympathetic activity. It has been found that spectral analysis of heart rate variability can be used to determine the relative levels of sympathetic and parasympathetic activity in a subject. Heart rate variability refers to the changes in heart rate that occur during a sinus rhythm (i.e., with normally activated and conducted heartbeats) and is primarily due to the interaction of the sympathetic and parasympathetic nervous systems. Low frequency variation in heart rate is due to both parasympathetic (or vagal) and sympathetic activity, while high frequency variation is primarily due to only parasympathetic activity. The ratio of low frequency variation to high frequency variation can thus be used as an indicator of the level of autonomic balance.

In order to perform spectral analysis of heart rate variability, the implanted device is programmed to measure and collect the time intervals between successive ventricular senses, referred to as RR intervals, for a period of time or a specified number of beats. The resulting series of RR interval values can then be stored as a discrete signal and either used directly as indexed by heartbeat or resampled at a specified sampling frequency in order to equalize the time intervals. The RR interval signal can then be analyzed to determine its energies in defined high and low frequency bands. It has been found that the amount of signal power in a low frequency (LF) band ranging from 0.04 to 0.15 Hz is influenced by the levels of activity of both the sympathetic and parasympathetic nervous systems, while the amount of signal power in a high frequency band (HF) ranging from 0.15 to 0.40 Hz is primarily a function of parasympathetic activity. The ratio of the signal powers, designated as the LF/HF ratio, is thus a good indicator of the state of autonomic balance, with a high LF/HF ratio indicating increased sympathetic activity, for example. Although spectral analysis of an RR interval signal can be performed directly in the frequency domain, a time-domain technique for determining the signal power in defined high and low frequency bands is preferably used for reasons of computational economy. However, the state of autonomic balance is assessed, a threshold level can then be defined for triggering the stress reduction mode.

c. Electrical Alternans

Under certain circumstances, the pattern of electrical excitation of the human heart exhibits oscillations during successive heart beats. Such beat-to-beat oscillations may relate to the amplitude, duration, and/or morphology of myocardial action potentials as well as of externally recorded waveforms (e.g., an EKG) that reflect the depolarization and repolarization of the myocardium during a heart beat. This phenomena is referred to as electrical alternans and is usually indicative of a pathological state in which potentially dangerous cardiac arrhythmias are more likely to occur. The presence of electrical alternans may thus be used as a pre-arrhythmic condition for triggering the stress reduction mode, with the implantable cardiac rhythm management device configured to utilize its sensing channels to detect such electrical alternans. The sensing channels produce electrogram signals that reflect the electrical activity at a local cardiac site near which a sensing electrode is disposed, and such local electrical activity exhibits oscillations during electrical alternans. In one embodiment, the device detects the start of depolarization and the end of repolarization (i.e., corresponding to the Q wave and T wave, respectively, in a surface EKG) in an electrogram signal from a ventricular sensing channel and measures the time interval therebetween. The interval so measured corresponds to the action potential duration of the local cardiac site. The device may then detect the presence of electrical alternans when the difference between intervals measured during successive heart beats exceeds a specified threshold value and the difference persists for a specified length of time or number of beats. Other embodiments may process the electrogram signal to determine if oscillations exist with respect to other features such as amplitude or waveform morphology and then detect electrical alternans if the oscillations are of sufficient magnitude and duration. Electrical alternans may also be detected by processing of electrogram signals from atrial sensing channels.

Figure 3:
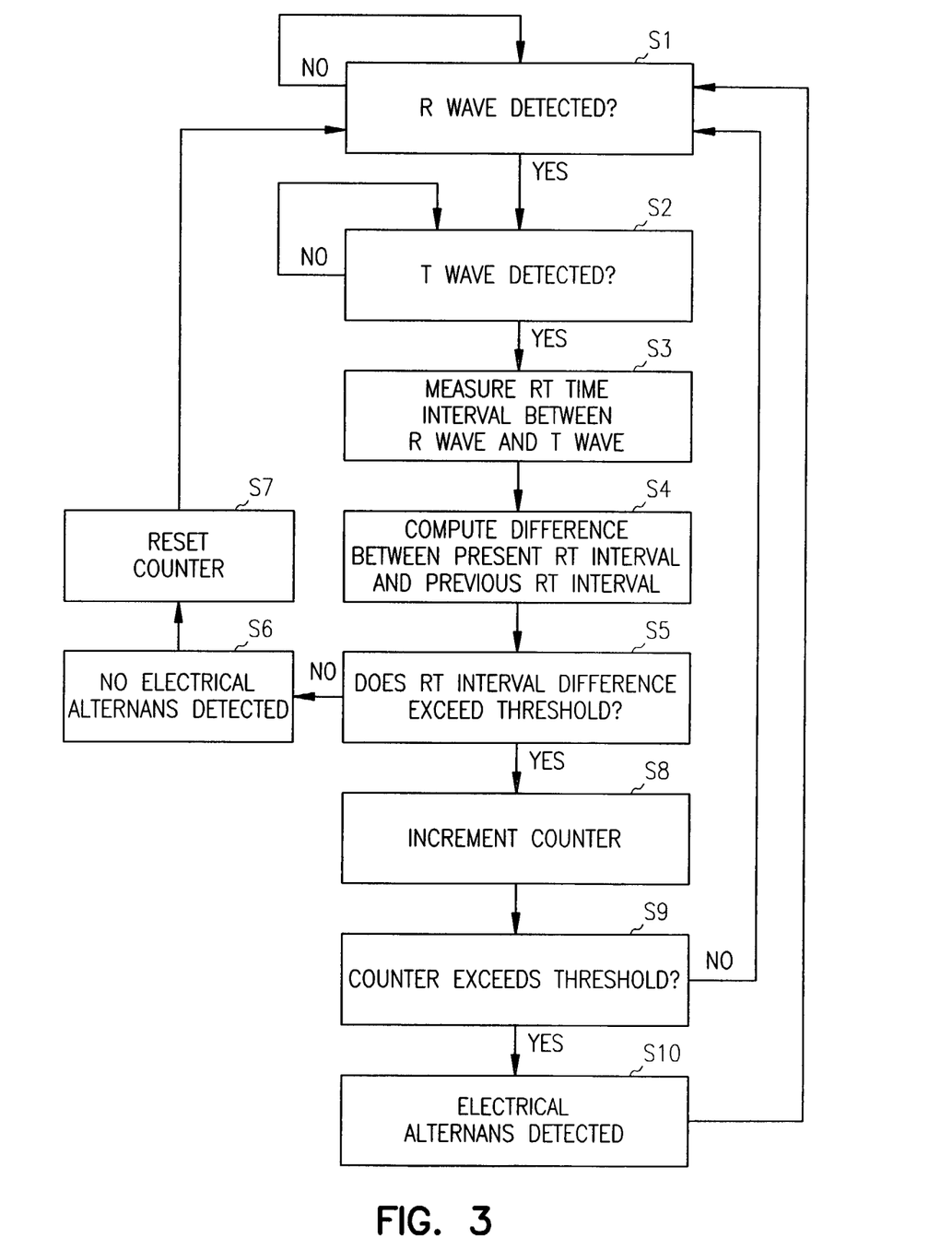
FIG. 3 illustrates an exemplary implementation of an algorithm for detecting electrical alternans.

FIG. 3 shows an exemplary algorithm for detecting electrical alternans based upon measurement of the R-T interval that can be implemented by the controller. At step S1, the device waits for an R wave (i.e., a ventricular sense). When an R wave is detected, the device then looks for a T wave in the ventricular sensing channel during an appropriate time window at step S2. When both R and T waves are detected during a cardiac cycle, the time interval between the two is measured at step S3. The difference between the R-T interval of the present cardiac cycle and the R-T interval of the previous cardiac cycle is then computed at step S4. If the R-T interval difference exceeds a specified threshold, as determined at step S5, a counter that keeps track of the number of consecutive R-T interval differences that exceed the threshold is incremented at step S8. Otherwise, a condition of no electrical alternans is detected at step S6, the counter is reset at step S7, and the device waits for the next R wave at step S1. If the R-T interval difference does exceed the threshold, after incrementing the counter at step S8, the counter's value is compared to a threshold count value at step S9. The threshold count value specifies the number of consecutive heart beats that the R-T interval difference must be above threshold before electrical alternans is detected. If the count exceeds the count threshold value, electrical alternans is detected at step S10. The device then returns to step S1 and measures the next R-T interval.

Electrical alternans is also highly correlated to oscillations in the mechanical function of the heart that result in alternations in pulse pressure, referred to as pulsus alternans. Since the pumping action of the heart is due to the electro-mechanical coupling between electrical depolarization of myocardial cells and their mechanical contraction, electrical alternans and pulsus alternans may be different manifestations of the same underlying phenomena in certain cases. Another way of detecting electrical alternans, therefore, is for a properly equipped implantable device to measure parameters reflective of pulse pressure in order to ascertain if oscillations exist in those parameters. Such parameters may include the intensity of heart sounds as measured by an accelerometer and stroke volume as measured by an impedance measuring circuit.

5. Stress Reduction Mode for Arrhythmia Prevention

As described above, one or more myocardial pacing sites identified as stressed may be mechanically unloaded during systole by delivering one or more pacing pulses in a manner such that the stressed site or sites are pre-excited relative to other regions of the myocardium. Such pacing subjects the stressed sites to a lessened preload and afterload during systole, thus reducing the wall stress. Pacing for myocardial wall stress reduction in order to prevent arrhythmias may be delivered in accordance with a programmed bradycardia pacing mode and thus also provide therapy for bradycardia as well. Such pacing also may or may not include multi-site pacing for purpose of also providing cardiac resynchronization therapy. What effects localized stress reduction is the pre-excitation of one or more myocardial regions relative to other regions during systole. This may be accomplished in certain situations with single-site pacing and in others with multi-site resynchronization pacing that also improves the pumping function of the heart. In the latter case, the pacing pulse output configuration and sequence that produces optimum resynchronization may or may not also deliver optimum therapy for reduction of myocardial wall stress.

In an exemplary embodiment, a device such as illustrated in FIG. 1 is configured with a plurality of pacing/sensing electrodes disposed in both ventricles at selected electrode sites so that pre-excitation pacing may be delivered to one or more of those sites in order to prevent ventricular arrhythmias. Alternative embodiments may be configured to deliver pre-excitation pacing to atrial sites in order to prevent atrial arrhythmias. The device may be programmed in a normal pacing mode to deliver pacing pulses to selected ones of the available pacing electrodes, referred to as a pulse output configuration, and in a specified time sequence, referred to as a pulse output sequence. Upon detection of a pre-arrhythmic condition, the device is programmed to initiate stress reduction pacing at selected one or ones of the available electrode sites that have been pre-identified as stressed sites. Switching to the stress reduction mode may include modifying the pulse output configuration by selecting different pacing channels and/or electrodes via switch matrix 70 for use in delivering pacing pulses from those used in the normal mode. For example, a pace may be delivered to a different site by interchanging which electrodes of a bipolar lead are the cathode and anode during bipolar pacing. The stress reduction mode may also have a different pulse output sequence in order to achieve the desired pre-excitation at a stressed site. The stress reduction mode may also include an adjustment of one or more of the escape intervals used in the particular bradycardia pacing mode employed to deliver pre-excitation paces to the ventricular sites such as a ventricular escape interval or an atrio-ventricular interval in the case of an atrial-tracking pacing mode. The escape intervals are adjusted in the stress reduction mode so that the pacing rate is above the measured intrinsic rate. Such overdrive pacing increases the frequency of paced cycles and hence increases the effectiveness of the stress reduction therapy in preventing arrhythmias.

In one example, the device normally delivers bradycardia pacing at a single ventricular site. Upon initiation of the stress reduction mode, the device switches the pacing configuration to deliver pacing pulses to another electrode site that has been identified as a stressed site. Single-site pacing that pre-excites the ventricle at this site results in the stressed site being excited before other regions of the ventricular myocardium as the wave of excitation spreads from the paced site. In another example, the device is programmed in the normal mode to deliver resynchronization pacing with multiple paces delivered to one or both ventricles during a cardiac cycle. Upon switching to the stress reduction mode, the pulse output configuration is modified, if necessary, to include one or more stressed sites, and the pulse output sequence is selected such that the stressed site or sites are excited before other regions as the wave of excitation spreads from the multiple pacing sites.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A cardiac rhythm management device, comprising:
sensing channels configured to sense cardiac electrical activity at a plurality of myocardial sites;
pacing channels configured to deliver pacing pulses to one or more of the plurality of myocardial sites;

a controller configured to control the delivery of pacing pulses in accordance with a programmed pacing mode;

circuitry configured to detect a pre-arrhythmic condition based upon a change in sensed cardiac electrical activity; and, circuitry configured to switch an operating mode of the device from a normal mode to a stress reduction mode upon detection of a pre-arrhythmic condition, where the stress reduction mode delivers pre-excitation pacing to particular identified stressed myocardial sites to an extent greater than the normal mode in order to reduce myocardial wall stress at the stressed sites.

2. The device of claim 1 wherein the circuitry configured to switch to a stress reduction mode modifies a pulse output sequence that defines an order in which pacing pulses are output during a pacing cycle, where the modified pulse output sequence excites an identified stressed myocardial site before other myocardial regions during systole.

3. The device of claim 1 wherein the circuitry configured to switch to a stress reduction mode modifies a pulse output configuration that defines which pacing channels are used during a pacing cycle such that an identified stressed site is excited before other myocardial regions during systole.

4. The device of claim 2 wherein the circuitry configured to switch to a stress reduction mode modifies one or more pacing parameters in order to increase the frequency of pacing.

5. The device of claim 1 wherein the circuitry configured to detect a pre-arrhythmic condition is circuitry to detect electrical alternans.

6. The device of claim 1 wherein the circuitry configured to detect a pre-arrhythmic condition is circuitry to perform spectral analysis of heart rate variability.

7. The device of claim 1 wherein the circuitry configured to detect a pre-arrhythmic condition is circuitry to measure ectopic beat frequency.

8. The device of claim 1 further comprising:

circuitry configured to measure activation-recovery intervals at a plurality of myocardial sites indicative of myocardial wall stress; and, circuitry configured to identify one or more stressed myocardial sites based upon the measured activation-recovery intervals.

9. The device of claim 8 further comprising circuitry configured to measure an activation-recovery interval as the time between a detected depolarization and a detected repolarization in an electrogram generated by a sensing channel.

10. A method for operating a cardiac rhythm management device, comprising:

sensing cardiac electrical activity at a plurality of myocardial sites;

delivering pacing pulses to one or more of the plurality of myocardial sites in accordance with a programmed pacing mode;

monitoring for changes in one or more physiological parameters derived from sensed cardiac electrical activity in order to detect a pre-arrhythmic condition; and, switching an operating mode of the device from a normal mode to a stress reduction mode upon detection of a pre-arrhythmic condition, where the stress reduction mode delivers pre-excitation pacing to particular identified stressed myocardial sites to an extent greater than the normal mode in order to reduce myocardial wall stress at the stressed sites.

11. The method of claim 10 wherein switching to a stress reduction mode modifies a pulse output sequence that defines an order in which pacing pulses are output during a pacing cycle, where modified pulse output sequence excites an identified stressed myocardial site before other myocardial regions during systole.

12. The method of claim 10 wherein switching to a stress reduction mode modifies a pulse output configuration that defines which pacing channels of the device are used during a pacing cycle such that an identified stressed site is excited before other myocardial regions during systole.

13. The method of claim 10 wherein switching to a stress reduction mode modifies one or more pacing parameters in order to increase the frequency of pacing.

14. The method of claim 10 wherein a pre-arrhythmic condition is detected by detecting electrical alternans.

15. The method of claim 10 wherein a pre-arrhythmic condition is detected by performing spectral analysis of heart rate variability.

16. The method of claim 10 wherein a pre-arrhythmic condition is detected by measuring ectopic beat frequency.

17. The method of claim 10 further comprising:

measuring activation-recovery intervals at a plurality of myocardial sites indicative of myocardial wall stress; and, identifying one or more stressed myocardial sites based upon the measured activation-recovery intervals.

18. The method of claim 17 further comprising measuring an activation-recovery interval as the time between a detected depolarization and a detected repolarization in an electrogram generated by a sensing channel.

19. An apparatus, comprising:

means for sensing cardiac electrical activity at a plurality of myocardial sites;

means for delivering pacing pulses to one or more of the plurality of myocardial sites;

means for monitoring for changes one or more physiological parameters derived from sensed cardiac electrical activity in order to detect a pre-arrhythmic condition;

means for identifying stressed myocardial sites; and, means for initiating delivery of pre-excitation pacing to particular identified stressed myocardial sites in response to detection of a pre-arrhythmic condition, where the pre-excitation pacing excites an identified stressed myocardial site before other myocardial regions during systole.

* * * * *

UNITED STATES PATENT AND TRADEMARK OFFICE
CERTIFICATE OF CORRECTION

| | |
|---|---|
| PATENT NO. | : 7,065,405 B2 |
| APPLICATION NO. | : 10/298156 |
| DATED | : June 20, 2006 |
| INVENTOR(S) | : Pastore et al. |

It is certified that error appears in the above-identified patent and that said Letters Patent is hereby corrected as shown below:

In column 12, line 46, in Claim 19, after "changes" insert -- in --.

Signed and Sealed this

Third Day of October, 2006

JON W. DUDAS
*Director of the United States Patent and Trademark Office*